United States Patent
Xia et al.

(10) Patent No.: US 11,242,550 B2
(45) Date of Patent: Feb. 8, 2022

(54) HIGH-THROUGHPUT ENZYMATIC PREPARATION OF GLUCOSYLATED STEVIOL GLYCOSIDES UNDER PROGRAMMING TEMPERATURES

(71) Applicants: Jiangnan University, Wuxi (CN); DONGTAI HAORUI BIOTECHNOLOGY CO., LTD., Dongtai (CN)

(72) Inventors: Yongmei Xia, Wuxi (CN); Liping Zhu, Dongtai (CN); Yun Fang, Wuxi (CN); Xiang Liu, Wuxi (CN); Haijun Wang, Wuxi (CN)

(73) Assignees: Jiangnan University, Wuxi (CN); DONGTAI HAORUI BIOTECHNOLOGY CO., LTD., Dongtai (CN)

( * ) Notice: Subject to any disclaimer, the term of this patent is extended or adjusted under 35 U.S.C. 154(b) by 438 days.

(21) Appl. No.: 16/210,057

(22) Filed: Dec. 5, 2018

(65) Prior Publication Data

US 2019/0218585 A1 Jul. 18, 2019

Related U.S. Application Data

(63) Continuation of application No. PCT/CN2018/089939, filed on Jun. 5, 2018.

(30) Foreign Application Priority Data

Jan. 15, 2018 (CN) .......................... 201810036308.X

(51) Int. Cl.
C12P 19/18 (2006.01)
C12N 9/10 (2006.01)
C12P 19/56 (2006.01)

(52) U.S. Cl.
CPC ............ *C12P 19/56* (2013.01); *C12N 9/1074* (2013.01); *C12P 19/18* (2013.01); *C12Y 204/01019* (2013.01)

(58) Field of Classification Search
CPC ........... C12Y 204/01019; C12N 9/1074; C12P 19/56; C12P 19/18
See application file for complete search history.

(56) References Cited

U.S. PATENT DOCUMENTS

2013/0004979 A1* 1/2013 Thorson et al. ................ 435/15

FOREIGN PATENT DOCUMENTS

| CN | 101775425 A | 7/2010 | |
| CN | 102492757 A | 6/2012 | |
| KR | 20050097117 A | * 10/2005 | ............... C12N 1/20 |
| WO | WO 2012042508 A1 | * 5/2012 | ............. C07H 15/24 |

OTHER PUBLICATIONS

CN102492757A—Machine English translation by Google (total pp. 1-6), (2012). (Year: 2012).*
KR20050097117A—Machine English translation by Google (total pp. 1-8), (2005). (Year: 2005).*

* cited by examiner

*Primary Examiner* — Satyendra K Singh
(74) *Attorney, Agent, or Firm* — IPro, PLLC; Na Xu

(57) ABSTRACT

The present invention discloses a method for preparing glucosyl steviol glycosides through enzymatic catalysis under programming temperatures in high throughput, belonging to the technical field of biosynthesis of sweeteners. By using cyclodextrin glucosyltransferase from *Geobacillus* sp. as a catalyst, steviol glycosides as the glycosyl receptor and dextrin or oligosaccharide as the glycosyl donor, taking a calcium/barium ion salt bridge as the main stabilizer and combining with glycerol to adjust the conformation and binding domain openness of the enzyme, and utilizing transglucosylation and hydrolytic activities of amylase at variable temperatures in different stages, thereby preparing the glucosyl steviol glycosides through enzymatic catalysis under programming temperatures in high throughput. The technology of the present invention can improve the utilization rate of the enzyme, and obtain glucosyl steviol glycosides with good sweetness and good taste.

8 Claims, 2 Drawing Sheets

HIGH-THROUGHPUT ENZYMATIC PREPARATION OF GLUCOSYLATED STEVIOL GLYCOSIDES UNDER PROGRAMMING TEMPERATURES

TECHNICAL FIELD

The present invention relates to high-throughput enzymatic preparation of glucosylated steviol glycosides under programming temperatures, belonging to the technical field of biosynthesis of sweeteners.

BACKGROUND

Steviol glycosides are generic names of glucoside molecules in *stevia* extract; they are composed of sweet hydrophilic glycosyl and hydrophobic steviol aglycone, and about 40 derivatives have been identified. Among them, rebaudioside A (RA), rebaudioside D and rebaudioside M have better taste, while stevioside (St), rebaudioside C and other low-molecular weight steviol glycosides have a slight bitterness or liquorice root aftertaste, and this slightly bitter aftertaste reduces their quality as a natural sweetener. Steviol aglycone has a very poor taste and a severe bitter aftertaste, which gives the steviol glycosides a slightly bitter taste. Therefore, in addition to the bitter taste of the impurities affecting the taste of the steviol glycosides, the molecular structure of the steviol glycosides is an important factor in the production of bitter aftertaste. The improvement of the taste of steviol glycosides can be based on the cause of bitterness. On the one hand, the hydrophobic bitter impurities are removed, so the purity of steviol glycosides is improved, and especially the content of RA with the best taste sweetness is improved; on the other hand, the steviol glycosides are modified in the aspect of the molecular structure, and the glycosyl is introduced by enzymatic glycosylation or the like to improve the taste quality. Grafting other groups on the steviol glycosides so as to keep the peripheral groups away from the steviol aglycone makes it possible to improve the bitterness afterwards; for example, moderate glycosidation is performed on the steviol glycosides. Glycosylation or grafting steviol glycosides includes chemical catalysis, enzymatic catalysis and whole cell catalysis.

The enzyme used for grafting steviol glycosides is mainly glycosyltransferase, as like cyclodextrin glycosyltransferase (cyclodextrin glucosyl transferase) at present, and there are also some reports about glucosidase, fructofuranosidase and galactosidase.

For example, after cyclodextrin glucosyltransferase from *Bacillus pseudofirmus* catalyzed the transglucosylation of stevioside for 10 h, 9 products were obtained after purification. The structural analysis showed that 1 to 3 glucosyl groups were respectively linked with α-1,4 glycosidic bonds at C-13 site of stevioside; when 1 or 2 glucosyl groups were linked at C-13 site, the taste quality was improved compared with St; and when three glucosyl groups were linked at C-13 site, the sweetness was reduced (Fukunaga, 1989). Lobov et al. used commercially available glucosylase to screen out pullulanase and fungal amylase (Biozyme L) for the transglucosylation of steviol glycosides to respectively obtain three products; however, the reaction took long time and the product yield was less than 10% (Lobov, 1991). Abelyan used cyclodextrin as a glycosyl donor to obtain nine transglycosylation products, two of which had better sweet taste characteristics, but had lower yield and a total yield of 11.6% (Abelyan V A, 2004). Kochikyan used six strains to produce different kinds of cyclodextrin glucosyltransferases, and liquefied starch as a glycosyl donor to catalyze transglycosylation of stevioside, so as to obtain seven transglycosylation products (Kochikyan V T, 2006). For the first time, Jaitak et al. applied a microwave-assisted method to enzymatic modification of steviol glycosides; and by using β-cyclodextrin as a glycosyl donor, the β-cyclodextrin glucosyltransferase derived from *Bacillus firmus* reacted in a phosphate buffer solution, of which the pH is 7.0, with a microwave power of 80 W and a reaction temperature of 50° C. to mainly obtain two α-1,4-glucosyl derivatives, 66% of 4'-O-α-D-glucosyl stevioside and 24% of 4"-O-α-D-maltosyl stevioside, so the bitter taste of steviol glycosides was significantly reduced (Jaitak V, 2009). Yamamoto et al. used cyclodextrin glucosyltransferase to catalyze the α-1,6 site transglycosylation reaction of steviol glycosides, and the steviol glycosides and starch reacted under the catalytic action of cyclodextrin glucosyltransferase for 4 h to obtain monosubstituted and disubstituted glucose graft products, with the yield being 35.7% and 42.9% respectively. After studying the reaction mechanism, it was concluded that the reason why the α-1,6 site transglycosylation was weaker than α-1,4 site transglycosylation was the linkage manner of glucosyl group on the glycosyl receptor (Yamamoto K, 1994). Tong Shumin used corn starch as a glycosyl donor at 50° C., and performed enzymatic modification on steviol glycosides by adding β-cyclodextrin glucosyltransferase; and after 48 h of reaction, the yield was 35.5% (Tong Shumin, 1998).

In our previous work, under low-throughput conditions, α-cyclodextrin glucosyltransferase Toruzyme 3.0 L and a mesophilic α-amylase were employed to catalyze modification of St with hydrolyzed starch, which yielded fourteen steviol glycoside derivatives; and the bitter aftertaste of the products was significantly improved, the taste was sweet. The optimal reaction conditions were: 0.01 g stevioside/mL, 0.01 g starch/mL, 60° C., mass ratio of starch to stevioside 1:1, 100 U/g stevioside of cyclodextrin glucosyltransferase, conversion rate of St reached 77.11% at 4 h. St-Glc1 and St-Glc2 with the highest sweetness had the highest yield. Thereafter, cyclodextrin and stevioside were used as substrates to react with an enzyme dosage of 10 U/g stevioside, and the conversion rate of stevioside reached up to 87.8% after 5 h. The conversion rate of stevioside was 59.9% under the optimal process conditions with corn starch hydrolysate; and under 50 W microwave radiation, 55° C., the mass ratio of β-cyclodextrin to stevioside of 1.5:1 and the enzyme dosage of 10 U/g stevioside, the reaction was carried out for 1 min, the conversion rate of stevioside reached 50.5%, but there were many products with high grafting degree and the taste was not good.

U.S. Pat. Nos. 4,219,571 and 7,807,206 used cyclodextrin glucosyltransferase from *Bacillus stearothermophilus* to give α-1,4 glucosyl derivatives having a polymerization degree of up to 10.

U.S. Pat. Nos. 8,257,948 and 8,31,8459 and Chinese Patent CN105899670 A used starch as a substrate, the starch was firstly treated with α-amylase and cyclodextrin glucosyltransferase, then cyclodextrin glucosyltransferase was added to the reaction solution for a second time, and after treatment with amylase or other carbohydrases, α-1,4-glucosyl derivatives were obtained, wherein the production process was complex and the cost was increased. In Chinese patent CN105899670 A, starch was added to water to form a starch suspension; a mixture of α-amylase and cyclodextrin glucosyltransferase was added to the starch suspension and incubated at about 75-80° C. for about 0.5 to 2 hours, and after the liquefied starch suspension was formed, the α-amylase was inactivated under low pH and heat treatment; then steviol glycosides were added to the liquefied starch suspension to form a reaction mixture, and a second batch of cyclodextrin glucosyltransferase was further added to the reaction mixture and incubated at about 5-125° C. for about 1 to 168 hours; and after addition of one or several carbohydrases, the reaction mixture was incubated at about 5-125° C. for about 0.0001-168 hours, the steviol glycoside composition including steviol glycoside derivatives having twenty or fewer α-1,4-glucosyl residues. The obtained product was decolorized by using an ion exchange resin or a membrane; the decolorized reaction mixture was contacted with macroporous resins to remove non-steviol glycoside compounds, and then the adsorbed steviol glycosides were eluted with an alcohol or an aqueous alcohol; desalting was carried out on the eluate by a column or membrane filled with ion exchange resin; the alcohol was removed from the eluate to obtain an aqueous eluate; and the aqueous eluate was concentrated and dried to obtain dried glucosyl steviol glycosides.

The cyclodextrin glucosyltransferase involved in the above methods belongs to carbohydrase. One characteristic of this enzyme is that the structural domain has a discrimination degree to multiple substrates, thus the throughput during the reaction is low, and the production efficiency needs to be improved.

Another characteristic of the cyclodextrin glucosyltransferase is poor thermo-stability. BC251 cyclodextrin glucosyltransferase, a cyclodextrin glucosyltransferase with known three-dimension structure, has a half-life of 10 min at 60° C., and *B. stearothermophilus* cyclodextrin glucosyltransferase has a half-life of 10 min at 75° C. The half-lives of *Thermococcus kodakaraensis* KOD122 and *Thermococcus strain* B1001 cyclodextrin glucosyltransferases were 20 min at 100° C. and 40 min at 110° C., respectively.

By comparing and summarizing the literature, it can be seen that salt bridge, pH and organic solvent can change the activity and heat stability of an enzyme, but there is no regularity to follow, nor universal significance-even the same enzyme needs different effective stabilizers in different reaction systems. When the cyclodextrin glucosyltransferase catalyzes the reaction, after the substrate is combined with the starch, the acidic active Glu257 in the enzyme gives the proton to the oxygen located between the subposition +1 and −1 glucoses, and after the bond is broken, the −1 glucose forms a transition state, this oxygen-carbon cation type transition state undergoes positive charge shift to form a double bond structure, thereby constituting a planar conformation; then the double bond structure is linked to the nucleophilic Asp229 via a β-glycosidic bond, the transition state forms a stable intermediate product, the +1 site is replaced by the donor itself or other glucoses, Glu257 activates the glucose molecule to attack the product intermediate, and the final product of the α-glycosidic bond is formed via the transition state. The reaction mechanism is a bisubstitution reaction (Uitdehaag, 2002). Therefore, it is necessary to take into account the characteristics of the above two amino acid residues when stimulating the thermostable ability of the enzyme by environmental factors.

Still another characteristic of the cyclodextrin glucosyltransferase is that it can simultaneously catalyze four reactions, such as transglucosylation and hydrolysis. Therefore, it is necessary to explore different substrates and catalytic environment, and reaction conditions can be selected as needed to make full use of various functions of the enzyme, so that multiple reactions are implemented with one enzyme.

In addition, since most of the enzyme-catalyzed reactions are external diffusion inhibition and even substrate inhibition, the production intensity, i.e., reaction throughput, is often low, and the reactant concentration reported in most literature is within 2%-5%, while a high-throughput reaction is a process that everyone pursues. Crude steviol glycosides have a higher solubility, and can achieve a higher reaction throughput more easily than single glycosides; however, high-quality glucosyl steviol glycosides requires the use of low-solubility steviol glycosides, which needs to be achieved by certain means.

Based on the above, there is a need for an improvement on the method for preparing glucosyl steviol glycosides, to improve the heat stability and reaction throughput of the enzyme and efficiently obtain high-conversion-rate low-grafting-degree glucosyl steviol glycosides.

SUMMARY

The object of the present invention is to improve the heat stability and reaction throughput of cyclodextrin glucosyltransferase in view of the above defects and disadvantages, so as to efficiently obtain high-conversion-rate low-grafting-degree glucosyl steviol glycosides by the reaction of higher-concentration substrates at a higher reaction temperature. According to the present invention, reactants are dissolved by forming an inclusion compound at a higher temperature, the temperature is lowered rapidly to reduce the molecular motion amplitude, a calcium/barium ion salt bridge is used as the main stabilizer and combined with polar small-molecule polyols such as glycerol or sorbitol to adjust the conformation and binding domain openness of the enzyme, a stabilizer-containing enzyme is added to catalyze the transglucosylation at a lower temperature, and while the transglucosylation is continuously catalyzed at a higher temperature, the hydrolysis of the high substituted product is catalyzed, thereby preparing the glucosyl steviol glycosides through enzymatic catalysis under programming temperatures in high throughput.

Specifically, using cyclodextrin glucosyltransferase derived from *Geobacillus* sp. as a catalyst, steviol glycosides as a glycosyl receptor and dextrin or oligosaccharide as a glycosyl donor, and utilizing transglucosidic and hydrolytic activities of the cyclodextrin glucosyltransferase at variable temperatures in different stages to prepare the glucosyl steviol glycosides in an aqueous phase under enzymatic catalysis under programming temperatures in high throughput.

More specifically, the steviol glycosides and the glycosyl donor are dissolved in water or a buffer solution with a certain pH environment at 80-85° C., the mass concentration of the steviol glycoside aqueous solution being 10%-25% and the mass ratio of the steviol glycosides to the glycosyl donor being (1:0.3)-(1:1.1), the system is quickly cooled to 60-65° C. after the dissolution is completed, cyclodextrin glucosyltransferase (10-100 U/g steviol glycoside) and an enzyme stabilizer are added, the temperature is kept to start to react for 0.5-5 h, and the temperature is raised to 70-76° C. to react for 8-24 h and finally raised to 75-85° C. to react for 8-24 h until the change of the content of the raw material steviol glycosides is less than 0.1% per hour; and the product is directly spray-dried, or slightly concentrated and dried to obtain a glucosyl steviol glycoside crude product. The residual dextrin or other reducing sugar or the like can be removed by macroporous resins adsorption and then eluted with water.

Wherein the steviol glycosides are only derived from various *stevia* extracts and chemically or enzymatically transformed products thereof. The glycosyl donor is dextrin or oligosaccharide, wherein the dextrin is one or a mixture of two of maltodextrin, corn starch dextrin, cassava dextrin and various cyclodextrins; and the oligosaccharide is one or a mixture of multiple of maltose, maltotriose, raffinose and melibiose. The enzyme stabilizer is calcium/barium ion salt, such as one or a mixture of both of calcium chloride and barium chloride, in an amount of 0.1%-1% by mass of the enzyme protein. Water or a buffer solution with a certain pH environment refers to deionized water or a phosphoric acid-ammonium phosphate buffer solution (0.01M) with a pH of 5-6.5. The amount of the glycerin or sorbitol is 0.1%-5% by mass of the enzyme protein. The present invention greatly improves the sweetness quality of the steviol glycosides, ensures the high efficiency and utilization ratio of the hydrolase, lowers the production cost of the glucosyl steviol glycosides, and obtains the glucosyl steviol glycosides with good sweetness and good taste.

Wherein the cyclodextrin glucosyltransferase is derived from *Geobacillus* sp., for example, from *Geobacillus thermoglucosidasius* (ATCC 43742 or CGMCC1.10851), or *Geobacillus tepidamans* (ATCC BAA-942), or *Geobacillus thermoleovorans* (CGMCC1.8647 or ATCC 43513), which has commonality of good α-amylase activity. According to an implementation of the present invention, the α-amylase activity is 163.7 U/mL, the β-amylase activity is 42.3 U/mL, the α-cyclase activity of the cyclodextrin glucosyltransferase is 83.1 U/mL, and the β-cyclase activity is 57.4 U/mL.

The present invention discloses a method for preparing glucosyl steviol glycosides through enzymatic catalysis under programming temperatures in high throughput. With no need for inactivation and decolorization sections, the method has the advantages of simple process and high throughput, improves the sweetness quality of the steviol glycosides, ensures the high efficiency and utilization ratio of the hydrolase, increases the conversion rate of raw materials, ensures that the enzyme can remain active for a long time, lowers the production cost of the glucosyl steviol glycosides and obtains the glucosyl steviol glycosides with good sweetness and good taste.

DETAILED DESCRIPTION

Figure 1:
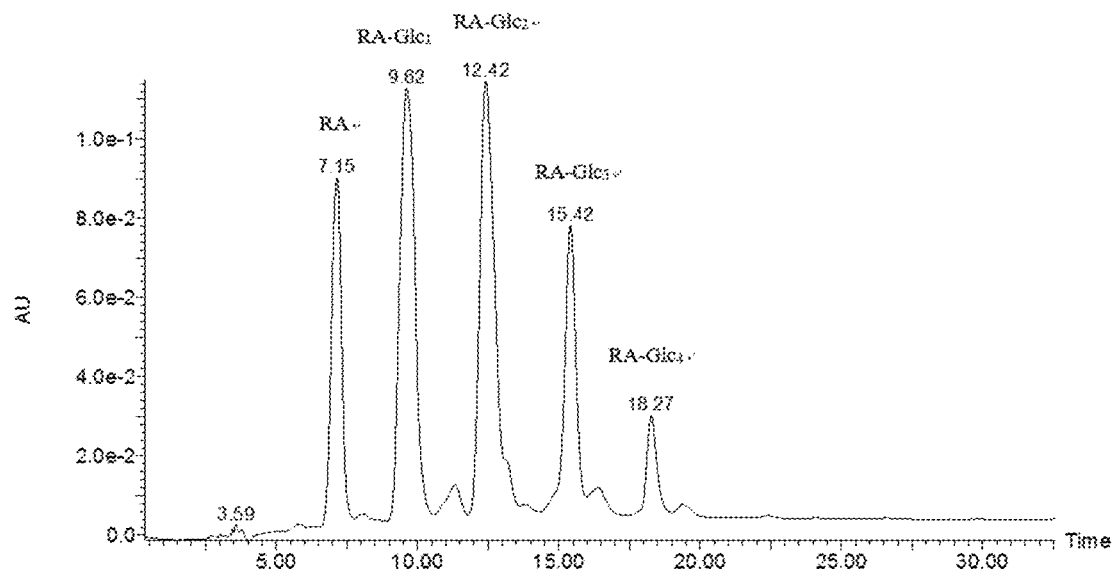
FIG. 1 HPLC chromatogram of the glucosyl rebaudioside A.

Analytical Method and Calculation:

(1) Quantitative analysis of unreacted steviol glycosides is based on the analysis and detection method of steviol glycosides presented in GB2760-2014 or JECFA2016.

(2) Qualitative analysis of glucosyl steviol glycosides: the transglucosylation product is qualitatively determined by a liquid chromatography tandem quadrupole time-of-flight mass spectrometer. The detection conditions are as follows: ACQUITY UPLC BEH HILIC amino column, column temperature 30° C., gradient elution under acetonitrile: water=80:20 (2 min)-50:50 (30 min) (v/v), injection volume 1 μL, injection concentration 5 mg/mL, flow rate 0.3 mL/min; the mass spectrometry condition is a collision voltage of 6 eV, and the ionization manner: electrospray ionization (ESI), negative ion detection mode, molecular weight range: 200-2000.

(3) Quantitative analysis of glucosyl steviol glycosides is based on the analysis and detection method of glucosyl steviol glycosides in the supplemental document of National Health and Family Planning Commission of the People's Republic of China in GB2760-2014.

(4) The α-amylase activity is determined by the α-amylase activity determination method of α-amylase preparation in Chinese Standard GB/T 24401-2009.

(5) The β-amylase activity is determined by a DNS (3,5-dinitrosalicylic acid) method, see P. Bernfeld, "Amylase, α and β," in Methods in Enzymology, S. P. Colowick and N. O. Kaplan, Eds., pp. 149-158, Academic Press, New York, N.Y., USA, 1955.

(6) Determination of cyclodextrin glucosyltransferase α- or β-cyclase activity:

0.1 mL of an appropriately diluted enzyme solution is added to a test tube containing 2 mL of a 1% (wt) soluble starch solution previously prepared with 10 mM phosphate buffer solution (pH 6.5). After reacting at 60° C. for 10 min, 1 mL of hydrochloric acid (1 mol/L) is added to stop the reaction, and the solution is rapidly cooled to room temperature.

When determining the α-cyclase activity, 0.2 mL of a 0.5 mM methyl orange solution prepared with 10 mM phosphate buffer solution is added to the above solution, and allowed to stand at room temperature for 15 min, and the absorbance $A_{505}$ at 505 nm is determined.

When determining the β-cyclase activity, 3.5 mL of a NaOH aqueous solution (30 mM) is added to the above solution, and 0.5 mL of a 0.02% (wt) phenolphthalein solution prepared with a 5 mM $Na_2CO_3$ solution is added, and allowed to stand at room temperature for 15 min, and the absorbance $A_{550}$ at 550 nm is determined.

Then, respectively referring to the standard curves of $A_{505}$ with respect to α-cyclodextrin concentration and $A_{550}$ with respect to β-cyclodextrin concentration, the α- or β-cyclodextrin contents of the solution are respectively calculated. One α- or β-cyclase unit is defined as the number of μmol that produces α- or β-cyclodextrin per minute under the above conditions.

Example 1 Preparation of Cyclodextrin Glucosyltransferase (CGTase)

A strain of *Geobacillus* sp. (*Geobacillus thermoglucosidasius*, ATCC 43742) was used as a production strain, inoculated at an inoculum size of 8% and followed by batch fermentation. A culture medium was composed of glucose 0.8%, lactose 0.05%, peptone 1.2%, yeast extract 2.4%, $K_2HPO_4$ 0.3%, $KH_2PO_4$ 0.98%, and $CaCl_2$ 0.28%. When the dissolved oxygen reached to 85%, the culture medium was supplemented, and the temperature was controlled at 33-37° C. and the dissolved oxygen was maintained at 25%-30% in the growth phase of the thalluses; when the $OD_{600}$ of the thalluses reached 25, 1% glycine (mass volume fraction) was supplemented; when the $OD_{600}$ of the thalluses reached 50, the temperature was lowered to 23-27° C. and 0.2-0.4 $g \cdot l^{-1} \cdot h^{-1}$ lactose was continuously added, and meanwhile, the culture medium was supplemented in a gradient descent manner; after 30 hours of fermentation and culture, the fermentation was terminated, and after removing the thalluses by centrifugation, the fermentation liquid was concentrated 10 times, wherein the α-amylase activity was 163.7 U/mL, the β-amylase activity was 42.3 U/mL, the α-cyclase activity of the cyclodextrin glucosyltransferase was 83.1 U/mL and the β-cyclase activity was 57.4 U/mL. When used as following cases, it is measured based on the α-cyclase activity of the cyclodextrin glucosyltransferase.

Example 2 Preparation of Glucosyl Steviol Glycosides with Cassava Dextrin and Rebaudioside A 100 kg of water was added to a jacketed reactor, and after heating to 85° C., 15 kg of cassava dextrin and 15 kg of rebaudioside A (HPLC content 98%) were sequentially added and stirred to dissolve. After being fully dissolved, the system was rapidly cooled to 65° C., and an aqueous solution containing 5 mL of 1% calcium chloride and barium chloride (mass ratio 0.2:1), 4 g of glycerin and 250 kU of a solution of the cyclodextrin glucosyltransferase obtained from Example 1 was added to the above jacketed reactor while stirring. The reaction was carried out at 65° C. for 3 h, then the temperature was raised to 75° C. to react for 24 h, then the temperature was raised to 80° C. to react for 10 h, and the reaction was terminated thereafter. The product was directly spray-dried to obtain the glucosyl steviol glycosides having a moisture content of 2.1%, and the product can be directly used without decolorization for a product which does not require a total glycoside content being not less than 95%. The content of rebaudioside A in the product was 2.9%.

Comparative Example 1 Preparation of Glucosyl Steviol Glycosides in the Absence of Stabilizer 100 kg of water was added to a jacketed reactor, and after heating to 85° C., 15 kg of cassava dextrin and 15 kg of rebaudioside A (HPLC content 98%) were sequentially added and stirred to dissolve. After being fully dissolved, the system was rapidly cooled to 65° C., and a solution containing 250 kU of a solution of the cyclodextrin glucosyltransferase obtained from Example 1 was added to the above jacketed reactor while stirring. The reaction was carried out at 65° C. for 3 h, then the temperature was raised to 75° C. to react for 24 h, then the temperature was raised to 80° C. to react for 10 h, and the reaction was terminated therafter. The product was directly spray-dried or slightly concentrated and dried to obtain the glucosyl steviol glycosides having a moisture content of 2.2%, wherein the content of rebaudioside A in the product was 5.2%.

Comparative Example 2 Preparation of Glucosyl Steviol Glycosides at Constant Temperature in the Absence of Stabilizer 100 kg of water was added to a jacketed reactor, and after heating to 75° C., 15 kg of cassava dextrin and 15 kg of rebaudioside A (HPLC content 98%) were sequentially added and stirred to dissolve. After being fully dissolved, 250 kU of a solution of the cyclodextrin glucosyltransferase obtained in Example 1 was added to the above jacketed reactor while stirring. The reaction was carried out at 75° C. for 48 h, and then terminated. The product was directly spray-dried to obtain the glucosyl steviol glycosides having a moisture content of 2.2%, wherein the content of rebaudioside A in the product was 6.1%.

Figure 2:
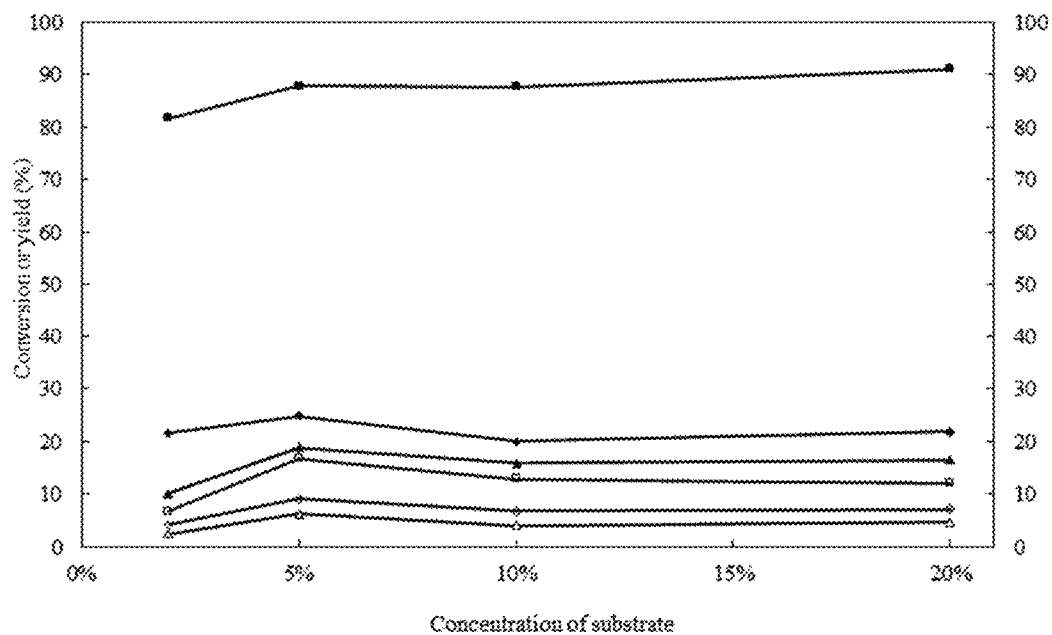
FIG. 2 Effect of substrate concentration on conversion rate of steviol glycosides and yield of each product; ■: St, ◆: St-Glc1, ▲: St-Glc2, □: St-Glc3, ◇: St-Glc4, △: St-Glc5. St refers to stevioside; St-Glcx refers to stevioside grafted x mol of glucosyl residues.

Comparative Example 3 Effect of Steviol Glycoside Concentration on Preparation of Glucosyl Steviol Glycosides in the Absence of Stabilizer FIG. 2 shows the effect of concentration of steviol glycosides on preparation of glucosyl steviol glycosides in the absence of a stabilizer at constant temperature with stevioside as an example. Under the conditions of stevioside:β-cyclodextrin=1.06:1, 60° C. and enzyme amount of 10 U/g glucoside, after the reaction is carried out for 5 h at different concentrations, the substrate concentration is positively correlated with the reaction rate in the low concentration range, and when the substrate concentration exceeds the optimum substrate concentration (5%), the conversion rate of stevioside and the yield of glucosyl steviol glycosides are lowered because of the inhibiting action of the substrate. The conversion rate of stevioside and the yield of glucosyl steviol glycosides are calculated based on the concentration of the corresponding compound in the reactants and theoretical values.

Example 3 Preparation of Glucosyl Steviol Glycosides with β-Cyclodextrin and Rebaudioside A as Raw Materials 100 kg of water was added to a jacketed reactor, and after heating to 82° C., 10 kg of β-cyclodextrin and 25 kg of rebaudioside A (HPLC content 97%) were sequentially added and stirred to dissolve. After being fully dissolved, the system was rapidly cooled to 60° C., and an aqueous solution containing 10 mL of 1% calcium chloride and barium chloride (mass ratio 0.5:1), 2 g of glycerin, 2 g of sorbitol and 1000 kU of a solution of the cyclodextrin glucosyltransferase obtained in Example 1 was added to the above jacketed reactor while stirring. The reaction was carried out at 60° C. for 3 h, then the temperature was raised to 74° C. to react for 15 h, then the temperature was raised to 80° C. to react for 8 h, and the reaction was terminated. The product was directly spray-dried to obtain the glucosyl steviol glycosides having a moisture content of 2.0%, and the product can be directly used without decolorization for a product which does not require a total glycoside content being not less than 95%. The content of rebaudioside A in the product was 2.2%. The product was eluted with macroporous resin column until the total glycoside content was about 96%, wherein the content of rebaudioside A in the product was 3.97%.

Example 4 Preparation of Glucosyl Steviol Glycosides with Maltodextrin and Steviol Glycosides Obtained as Byproduct from Recrystallization of Rebaudioside A 100 kg of 0.01M phosphate buffer solution with the pH being 5.8 was added to a jacketed reactor, and after heating to 80° C., 10 kg of maltodextrin (DE value 16) and 20 kg of steviol glycosides obtained as byproduct from recrystallization of Rebaudioside A (HPLC content 97% of total steviol glycosides) were sequentially added and stirred to dissolve. After being fully dissolved, the system was rapidly cooled to 62° C., and an aqueous solution containing 20 mL of 0.8% barium chloride, 8 g of glycerin and 1250 kU of a solution of the cyclodextrin glucosyltransferase obtained in Example 1 was added to the above jacketed reactor while stirring. The reaction was carried out at 65° C. for 3 h, then the temperature was raised to 75° C. to react for 24 h, then the temperature was raised to 80° C. to react for 18 h, and the reaction was terminated. The product was concentrated and microwave-dried to obtain the glucosyl steviol glycosides having a moisture content of 2.8%, and the product can be directly used without decolorization for a product which does not require a total glycoside content being not less than 95%. The content of unconverted steviol glycosides in the product was 2.7%. The product was eluted with macroporous resin column until the total glycoside content was about 96%, wherein the content of unconverted steviol glycosides in the product was 5.4%.

Example 5 Preparation of Glucosyl Steviol Glycosides with Corn Starch and Stevioside as Raw Materials 100 kg of water was added to a jacketed reactor, and after heating to 80° C., 10 kg of corn starch and 12 kg of stevioside (HPLC content 95%) were sequentially added and stirred to dissolve. After being fully dissolved, the system was rapidly cooled to 65° C., and an aqueous solution containing 10 mL of 0.5% barium chloride, 3 g of glycerin and 250 kU of a solution of the cyclodextrin glucosyltransferase obtained in Example 1 was added to the above jacketed reactor while stirring. The reaction was carried out at 65° C. for 3 h, then the temperature was raised to 72° C. to react for 15 h, then the temperature was raised to 80° C. to react for 8 h, and the reaction was terminated. The product was directly spray-dried to obtain the glucosyl steviol glycosides having a moisture content of 2.3%, and the product can be directly used without decolorization for a product which does not require a total glycoside content being not less than 95%. The content of stevioside in the product was 2.7%.

Figure 3:
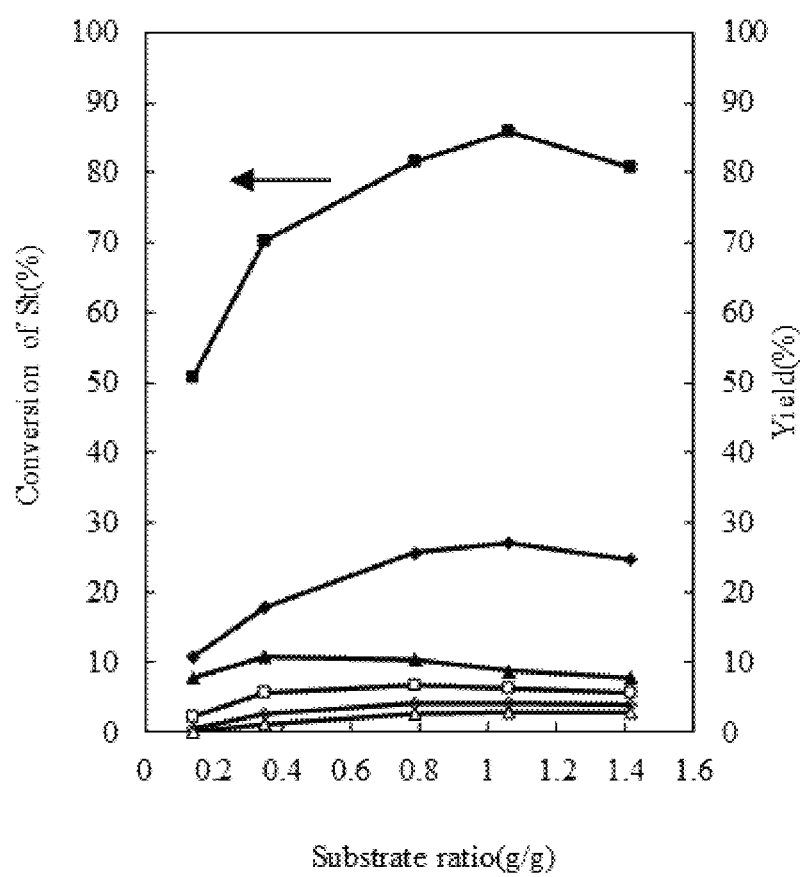
FIG. 3 Effect of ratio of steviol glycoside: glycosyl donor on conversion rate of steviol glycosides and yield of each product; ■: St, ◆: St-Glc1, ▲: St-Glc2, □: St-Glc3, ◇: St-Glc4, △: St-Glc5.

Comparative Example 4 Effect of Steviol Glycoside:Glycosyl Donor Ratio on Preparation of Glucosyl Steviol Glycosides in the Absence of Stabilizer FIG. 3 shows the effect of the glucoside:glycosyl donor ratio on preparation of glucosyl steviol glycosides at constant temperature in the absence of a stabilizer with stevioside and β-cyclodextrin as an example: When the temperature is 60° C., the enzyme amount is 10 U/g and the β-cyclodextrin:stevioside ratio is 1.06:1, the conversion rate of stevioside is the highest. The conversion rate of stevioside is calculated based on the concentration of the corresponding compound in the reactants and theoretical values.

Example 6 Preparation of Glucosyl Steviol Glycosides with Maltotriose and Steviol Glycosides Obtained as Byproduct from Recrystallization of Rebaudioside A as Raw Materials 100 kg of water was added to a jacketed reactor, and after heating to 80° C., 18 kg of maltotriose and 20 kg of steviol glycosides obtained as byproduct from recrystallization of Rebaudioside A (HPLC content 97%) were sequentially added and stirred to dissolve. After being fully dissolved, the system was rapidly cooled to 65° C., and an aqueous solution containing 20 mL of 1% calcium chloride and barium chloride (mass ratio 1:0.5), 8 g of sorbitol and 1250 kU of a solution of the cyclodextrin glucosyltransferase obtained in Example 1 was added to the above jacketed reactor while stirring. The reaction was carried out at 65° C. for 5 h, then the temperature was raised to 75° C. to react for 14 h, then the temperature was raised to 80° C. to react for 6 h, and the reaction was terminated. The product was directly spray-dried to obtain the glucosyl steviol glycosides having a moisture content of 2.1%, and the product can be directly used without decolorization for a product which does not require a total glycoside content being not less than 95%. The content of unconverted steviol glycosides in the product was 3.7%. The product was eluted with macroporous resin column until the total glycoside content was about 96%, wherein the content of unconverted steviol glycosides in the product was 5.6%.

What is claimed is:

1. A method for high throughput synthesis and production of glucosyl steviol glycosides which comprises:
   incubating cyclodextrin glucosyltransferase, steviol glycosides, dextrin or oligosaccharide, salt and polyol in an aqueous reaction mixture using the following steps:
   (a) dissolving the steviol glycosides and the dextrin or the oligosaccharide in water or a buffer solution at 80 to 85° C.,
   (b) cooling to 60 to 65° C.,
   (c) adding the salt and the polyol, and 10 to 100 U/g steviol glycoside of the cyclodextrin glucosyltransferase,
   (d) maintaining the temperature at 60 to 65° C. for 0.5 to 5 hours,
   (e) raising the temperature to 70 to 76° C. for 8 to 24 hours, and then
   (f) raising the temperature further to 75 to 85° C. for 8 to 24 hours until a change in the content of steviol glycosides in the reaction mixture is less than 0.1% per hour;
   wherein the steviol glycosides are rebaudioside A.

2. The method according to claim 1, wherein the cyclodextrin glucosyltransferase is a cyclodextrin glucosyltransferase or an immobilized enzyme thereof produced by a strain of *Geobacillus* sp.

3. The method according to claim 1, wherein a mass concentration of steviol glycoside is 10% to 25%, and a mass ratio of the steviol glycosides to the dextrin or oligosaccharide is 1:0.3 to 1:1.1.

4. The method according to claim 1, wherein the steviol glycosides are any one or a mixture of steviol glycosides extracted from *stevia*, or obtained by a fermentation method or by an enzymatic method.

5. The method according to claim 1,
   wherein the dextrin is any one or a mixture of maltodextrin, corn starch dextrin, cassava dextrin, and various cyclodextrins; and
   wherein the oligosaccharide is any one or a mixture of maltose, maltotriose, raffinose, and melibiose.

6. The method according to claim 1, wherein the salt is any one or a mixture of calcium chloride and barium chloride, present in an amount of 0.1% to 1% by mass of the cyclodextrin glucosyltransferase; and
   wherein the polyol is any one or a mixture of glycerol and sorbitol, present in amount of 0.1% to 5% by mass of the cylodextrin glucosyltransferase.

7. The method according to claim 1, wherein the water or the buffer solution is deionized water or a phosphoric acid-ammonium phosphate buffer solution with a pH in the range of 5 to 6.5.

8. The method according to claim 1, further comprising:
spray drying, or concentrating and drying the glucosyl steviol glycosides produced to obtain a glucosyl steviol glycoside crude product, and
removing residual dextrin or other reducing sugar by macroporous resin adsorption followed by elution with water.

* * * * *